(12) United States Patent
Akiyama et al.

(10) Patent No.: US 7,297,779 B2
(45) Date of Patent: Nov. 20, 2007

(54) COLON CANCER METASTASIS INHIBITOR

(75) Inventors: Tetsu Akiyama, Tama (JP); Yoshihiro Kawasaki, Tokyo (JP); Rina Esashi, Houston, TX (US)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/537,001

(22) PCT Filed: Aug. 19, 2003

(86) PCT No.: PCT/JP03/10449

§ 371 (c)(1),
(2), (4) Date: Nov. 3, 2005

(87) PCT Pub. No.: WO2004/047867

PCT Pub. Date: Jun. 10, 2004

(65) Prior Publication Data

US 2006/0067919 A1    Mar. 30, 2006

(30) Foreign Application Priority Data

Nov. 24, 2002    (JP) .............................. 2002-382083

(51) Int. Cl.
*C07H 21/02* (2006.01)
*C07H 21/04* (2006.01)
*A01N 43/04* (2006.01)
*A61K 31/70* (2006.01)
(52) U.S. Cl. ........................ 536/23.1; 536/24.5; 514/44
(58) Field of Classification Search .............. 536/24.5, 536/23.1; 514/44, 12; 435/6
See application file for complete search history.

(56) References Cited

U.S. PATENT DOCUMENTS

| 6,506,559 B1 * | 1/2003 | Fire et al. ........................ 435/6 |
| 2003/0073623 A1 * | 4/2003 | Drmanac et al. .............. 514/12 |
| 2003/0157531 A1 * | 8/2003 | Costa et al. .................... 435/6 |

FOREIGN PATENT DOCUMENTS

JP    2001-57888 A    6/2001

OTHER PUBLICATIONS

Senda et al., The tumor suppressor protein APC colocalizes with b-catenin in the colon epithelial cells, 1996, Biochemical & Biophysical Research Communications, vol. 223, pp. 329-334.*
Opalinska et al., Nucleic-acid therapeutics: Basic principles and recent applications, Jul. 2002, Nature Reviews Drug Discovery, vol. 1, pp. 503-514.*
Patil et al., DNA-based therapeutics and DNA delivery systems: A comprehensive reivew, 2005, The AAPS Journal, vol. 7, pp. E61-E77.*
Kawasaki et al., "Mutated APC and Asef are Involved in the Migration of Colorectal Tumor Cells," Nature Cell Biology, vol. 5, Mar. 2003 (pp. 211-215).
Jimbo et al., "A New Stage of a Study of APC Protein," Molecular Medicine, vol. 39, No. 11, 2002 (pp. 1274-1279) (with partial English translation).
Akiyama, "The Tumor Suppressor Gene Product APC and Asef," Journal of Clinical and Experimental Medicine, vol. 205, No. 13, 2003 (p. 1001) (with partial English translation).
Kawasaki et al., "A Mutated APC/Asef Complex is Involved in Motility of Cololectal Cancer Cells," Supplement of Japanese Journal of Cancer Research, No. 3048, vol. 61, 2002 (p. 111) (with partial English translation).
Kawasaki et al., "Asef, a Link Between the Tumor Suppressor APC and G-Protein Signaling," SCIENCE, vol. 289, Aug. 18, 2000 (pp. 1194-1197).
Kawasaki et al., "A Novel Function of the Tumor Suppressor Gene Product APC," Protein, Nucleic Acid and Enzyme, vol. 46, No. 3, 2001 (pp. 228-232) (with partial English translation).
Senda, "APC Tumor Suppressor Gene—Diversity of its Expression and Functions," Jpn. J. Clin. Electron Microsc., vol. 33, No. 2, 2001 (pp. 65-74) (with partial English translation).
Paddison et al., "Short Hairpin RNAs (shRNAs) Induce Sequence-Specific Silencing in Mammalian Cells," Genes & Development, vol. 16, No. 8, 2002 (pp. 948-958).
Jenuwein, "An RNA-Guided Pathway for the Epigenome," SCIENCE, vol. 297, Sep. 27, 2002 (pp. 2215-2218).
Kinzler et al., "Lessons from Hereditary Colorectal Cancer," CELL, vol. 87, Oct. 18, 1996 (pp. 159-170).
Fearnhead et al., "The ABC of APC," Human Molecular Genetics, vol. 10, No. 7, 2001 (pp. 721-733).
Bienz et al., "Linking Colorectal Cancer to Wnt Signaling," CELL, vol. 103, Oct. 13, 2000 (pp. 311-320).
Peifer et al., "Wnt Signaling in Oncogenesis and Embryogenesis—A Look Outside the Nucleus," SCIENCE, vol. 287, Mar. 3, 2000 (pp. 1606-1609).
Akiyama, "Wnt/β-Catenin Signaling," Cytokine & Growth Factor Reviews, vol. 11, 2000 (pp. 273-282).
Miyoshi et al., "Somatic Mutations of the APC Gene in Colorectal Tumors: Mutation Cluster Region in the APC Gene," Human Molecular Genetics, vol. 1, No. 4, 1992 (pp. 229-233).
Nagase et al., "Mutations of the APC (Adenomatous Polyposis Coli) Gene," Human Mutation, vol. 2, 1993 (pp. 425-434).
Molenaar et al., "XTcf-3 Transcription Factor Mediates β-Catenin-Induced Axis Formation in Xenopus Embryos," Cell, vol. 86, Aug. 9, 1996 (pp. 391-399).

(Continued)

*Primary Examiner*—Jon E. Angell
*Assistant Examiner*—Dana Shin
(74) *Attorney, Agent, or Firm*—Kilyk & Bowersox, P.L.L.C.

(57) ABSTRACT

The present invention provides an agent for inhibiting metastasis of colorectal cancer and a method for inhibiting metastasis of colorectal cancer, which inhibit the function of Asef (i.e., binding activity to the APC gene product or guanine nucleotide exchange factor activity) that binds to the gene product of the tumor suppressor gene APC that plays an important role in tumorigenesis and in developmental processes, and/or inhibit the expression of the Asef gene.

1 Claim, 4 Drawing Sheets

OTHER PUBLICATIONS

Behrens et al., "Functional Interaction of β-Catenin With the Transcription Factor LEF-1," NATURE, vol. 382, Aug. 15, 1996 (pp. 638-642).

Wong et al., "Forced Expression of the Tumor Suppressor Adenomatosis Polyposis Coli Protein Induces Disordered Cell Migration in the Intestinal Epithelium," Proc. Natl. Acad. Sci, USA, vol. 93, Sep. 1996 (pp. 9588-9593).

Oshima et al., "Morphological and Molecular Processes of Polyp Formation in $Apc^{\Delta 716}$ Knockout Mice," Cancer Research, vol. 57, May 1, 1997 (pp. 1644-1649).

International Search Report for PCT/JP03/10449 dated Dec. 2, 2003.

Translation of International Preliminary Report on Patentability for PCT/JP2003/010449 dated Sep. 29, 2005.

* cited by examiner

COLON CANCER METASTASIS INHIBITOR

This application is a National Stage Application of PCT/JP2003/010449, filed Aug. 19, 2003 and claims priority from Japanese Patent Application No. 2002-382083, filed Nov. 24, 2002, which is incorporated herein by reference in its entirety.

TECHNICAL FIELD

The present invention relates to a method for inhibiting metastasis of colorectal cancer and an agent for inhibiting metastasis of colorectal cancer, which are characterized by inhibiting the function of Asef (APC-stimulated guanine nucleotide exchange factor) and/or inhibiting the expression of Asef. More specifically, the present invention relates to an agent for inhibiting metastasis of colorectal cancer, an agent for inhibiting Asef, a pharmaceutical composition, an agent for preventing and/or treating colorectal cancer, a method for inhibiting metastasis of colorectal cancer, and a method for preventing and/or treating colorectal cancer, which are characterized by inhibiting the expression of Asef, inhibiting the binding of Asef to the gene product of APC (Adenomatous Polyposis Coli), or inhibiting the guanine nucleotide exchange factor (hereunder, referred to in abbreviated form as "GEF") activity of Asef.

BACKGROUND ART

Asef is a protein that was found by the present inventors as a colorectal tumor suppressor gene-associated protein M1, which has already been disclosed and for which a patent application has been filed (Patent Reference 1 and Non-patent Reference 1). The protein consists of 619 amino acid residues, and contains the Db1 homology (DH) domain, the pleckstrin homology (PH) domain and the Src homology 3 (SH3) domain in its amino acid sequence.

In terms of function, it is known that Asef has GEF activity specific for Rac. Rac belongs to the Rho family, which is one of the small GTP-binding protein families. More specifically, Asef binds to Rac to stimulate a GDP/GTP exchange reaction which results in the activation of Rac, thereby acting on NFκB, c-jun, SRE and the like, which are located downstream of the Rac related-intracellular signal transduction. The Rho family proteins play key roles in the reorganization of the acting network, thereby regulating cell migration and cell-cell adhesion. Therefore, there is a possibility that Asef induces cellular lamellipodia (lobopodium) or cell membrane ruffling and participates in cell migration and cell-cell adhesion.

It has been revealed that the binding of Asef to the gene product of the tumor suppressor gene APC via the armadillo repeat domain of the gene product. The GEF activity of Asef is positively regulated by the APC gene product. Actually, the induction of Asef-mediated cell membrane ruffling or lamellipodia formation by the APC gene product is observed in MDCK cells that are canine kidney-derived epithelial-like cells. Further, Asef accumulates at the tips of microtubules in motile cells similarly to the APC gene product. Therefore, Asef may hold the key to control cell migration when cells migrate from the crypt to the villus tip of the colon.

Meanwhile, the tumor suppressor gene APC (Non-patent Reference 2) has been isolated as a responsible gene for familial adenomatous polyposis (FAP). Mutation of the gene is observed in approximately 70% to 80% of sporadic colorectal cancers. The APC gene product (hereunder, referred to as "APC") is a giant protein of approximately 300 kDa that comprises 2,843 amino acid residues. APC contains an armadillo repeat domain in the amino acid sequence thereof that participates in protein-protein interaction. Most somatic APC mutations observed in colorectal tumor cells occur within its central region called the "mutation cluster region (MCR)" and result in the generation of truncated APCs that lack the binding sites for microtubules, EB 1 or hDLG, and at least some of the sites for β-catenin and Axin (Non-patent References 4, 5, 6, 7 and 8). However, the region of APC responsible for binding to Asef, the armadillo repeat domain, is retained in most mutant APCs (Non-patent References 6, 7 and 8). APC has a function to bind to β-catenin, one kind of oncogene product, to induce its degradation (Non-patent References 2, 3, 4, 5 and 6). β-catenin, which is a Wnt/Wingless signal transduction factor, binds to the cytoplasmic domain of cadherin and plays a role in cell adhesion, while it plays important roles in developmental processes and in tumorigenesis (Non-patent References 9 and 10).

The amino acid sequence of Asef and the nucleotide sequence of its gene have been deposited with GenBank under the accession number AB042199. Further, the amino acid sequence of APC and the nucleotide sequence of its gene have been deposited with GenBank under the accession number NM000038.

Documents referred to in this specification are listed hereunder:

Patent Reference 1: Japanese Patent Laid-Open No. 2001-057888.

Non-patent Reference 1: Kawasaki, Y., et al., Science, 2000, Vol. 289, p. 1194-1197.

Non-patent Reference 2: Kinzler, K. W., et al., Cell, 1996, Vol. 87, p. 159-170.

Non-patent Reference 3: Fearnhead, et al., Human Molecular Genetics, 2001, Vol. 10, p. 721-733.

Non-patent Reference 4: Bienz, M., et al., Cell, 2000, Vol. 103, p. 311-320.

Non-patent Reference 5: Perifer, M., et al., Science, 2000, Vol. 287, p. 1606-1609.

Non-patent Reference 6: Akiyama, T., Cytokine and Growth Factor Reviews, 2000, Vol. 11, p. 273-282.

Non-patent Reference 7: Miyoshi, Y., et al., Human Molecular Genetics, 1992, Vol. 1, p. 229-233.

Non-patent Reference 8: Nagawa, H., et al., Human Mutation, 1993, Vol. 2, p. 425-434.

Non-patent Reference 9: Cell, 1996, Vol. 86, p. 391-399.

Non-patent Reference 10: Nature, 1996, Vol. 382, p. 638-642.

Non-patent Reference 11: Wong, M. H., et al., Proceeding of national academy of science USA」 1996, Vol. 93, p. 9588-9593.

Non-patent Reference 12: Oshima, H., et al., Cancer Research, 1997, Vol. 57, p. 1644-1649.

Non-patent Reference 13: Paddison, P. J., et al., Genes and Development, 2002, Vol. 16, p. 948-958.

DISCLOSURE OF THE INVENTION

It is known that Asef binds to the gene product of the tumor suppressor gene APC which plays important roles in tumorigenesis and in developmental processes as described in the foregoing. However, the function of Asef in cells and the relation of Asef with diseases have not yet been clarified. To clarify the function of Asef and regulate the function thereof makes it possible to prevent and treat diseases attributable to Asef.

The present inventors hypothesized based on the GEF activity of Asef and its intracellular localization that Asef may participate in cell migration and cell-cell adhesion, and found that Asef promotes the motility of colorectal tumor cells in colorectal cancers, particularly in colorectal cancers in which APC mutations are observed, and participates in the metastasis. By utilizing this finding, the present inventors found that metastasis of colorectal cancer is inhibited by inhibiting the function of Asef and/or inhibiting the expression of the Asef gene, and thereby complete the present invention.

That is, one aspect of the present invention relates to an agent for inhibiting metastasis of colorectal cancer, wherein the agent inhibits the function of Asef and/or inhibits the expression of the Asef gene.

Another aspect of the present invention relates to an agent for inhibiting metastasis of colorectal cancer, wherein the agent inhibits the expression of the Asef gene.

A further aspect of the present invention relates to an agent for inhibiting metastasis of colorectal cancer, wherein the agent inhibits the binding of Asef to the gene product of APC.

A still further aspect of the present invention relates to an agent for inhibiting metastasis of colorectal cancer, wherein the agent inhibits the guanine nucleotide exchange factor activity of Asef.

A further aspect of the present invention relates to a method for inhibiting metastasis of colorectal cancer, wherein the method comprises inhibiting the function of Asef and/or inhibits the expression of the Asef gene.

A further aspect of the present invention relates to a method for inhibiting metastasis of colorectal cancer, wherein the method comprises inhibiting the expression of the Asef gene.

A still further aspect of the present invention relates to a method for inhibiting metastasis of colorectal cancer, wherein the method comprises inhibiting the binding of Asef to the gene product of APC.

A further aspect of the present invention relates to a method for inhibiting metastasis of colorectal cancer, wherein the method comprises inhibiting the guanine nucleotide exchange factor activity of Asef.

A further aspect of the present invention relates to an agent for inhibiting Asef, wherein the agent utilizes RNA interference for the expression of the Asef gene.

A still further aspect of the present invention relates to an agent for inhibiting Asef, comprising an oligonucleotide that exhibits an RNA interference effect on the expression of the Asef gene.

A further aspect of the present invention relates to an oligonucleotide having the nucleotide sequence set forth in SEQ ID NO: 1 in the sequence listing.

A further aspect of the present invention relates to an oligonucleotide having the nucleotide sequence set forth in SEQ ID NO: 2 in the sequence listing.

A still further aspect of the present invention relates to an oligonucleotide having the nucleotide sequence set forth in SEQ ID NO: 3 in the sequence listing.

A further aspect of the present invention relates to an oligonucleotide having the nucleotide sequence set forth in SEQ ID NO: 4 in the sequence listing.

A further aspect of the present invention relates to the preceding agent for inhibiting Asef, comprising an oligonucleotide having the nucleotide sequence set forth in SEQ ID NO: 1 or 3 in the sequence listing.

A still further aspect of the present invention relates to a method for inhibiting Asef, wherein the method utilizes RNA interference on the expression of the Asef gene.

A further aspect of the present invention relates to a method for inhibiting Asef, wherein the method comprises utilizing an oligonucleotide exhibiting an RNA interference effect on the expression of the Asef gene.

A further aspect of the present invention relates to the preceding method for inhibiting Asef, wherein the method comprises utilizing an oligonucleotide having the nucleotide sequence set forth in SEQ ID NO: 1 or 3 in the sequence listing.

A still further aspect of the present invention relates to an agent for inhibiting metastasis of colorectal cancer, comprising any one of the preceding agents for inhibiting Asef.

A further aspect of the present invention relates to an agent for inhibiting metastasis of colorectal cancer, comprising an oligonucleotide having the nucleotide sequence set forth in any one of SEQ ID NOS: 1 to 4 in the sequence listing.

A further aspect of the present invention relates to a method for inhibiting metastasis of colorectal cancer, wherein the method uses any one of the preceding agents for inhibiting Asef.

A still further aspect of the present invention relates to a method for inhibiting metastasis of colorectal cancer, wherein the method uses an oligonucleotide having the nucleotide sequence set forth in any one of SEQ ID NOS: 1 to 4 in the sequence listing.

A further aspect of the present invention relates to a pharmaceutical composition, comprising any one of the preceding agents for inhibiting metastasis of colorectal cancer, or any one of the agents for inhibiting Asef.

A further aspect of the present invention relates to an agent for preventing and/or treating colorectal cancer, comprising any one of the preceding agents for inhibiting metastasis of colorectal cancer, or any one of the agents for inhibiting Asef.

A still further aspect of the present invention relates to a method for preventing and/or treating colorectal cancer, wherein the method uses any one of the preceding agents for inhibiting metastasis of colorectal cancer, or any one of the agents for inhibiting Asef.

DETAILED DESCRIPTION OF THE INVENTION

Figure 1:
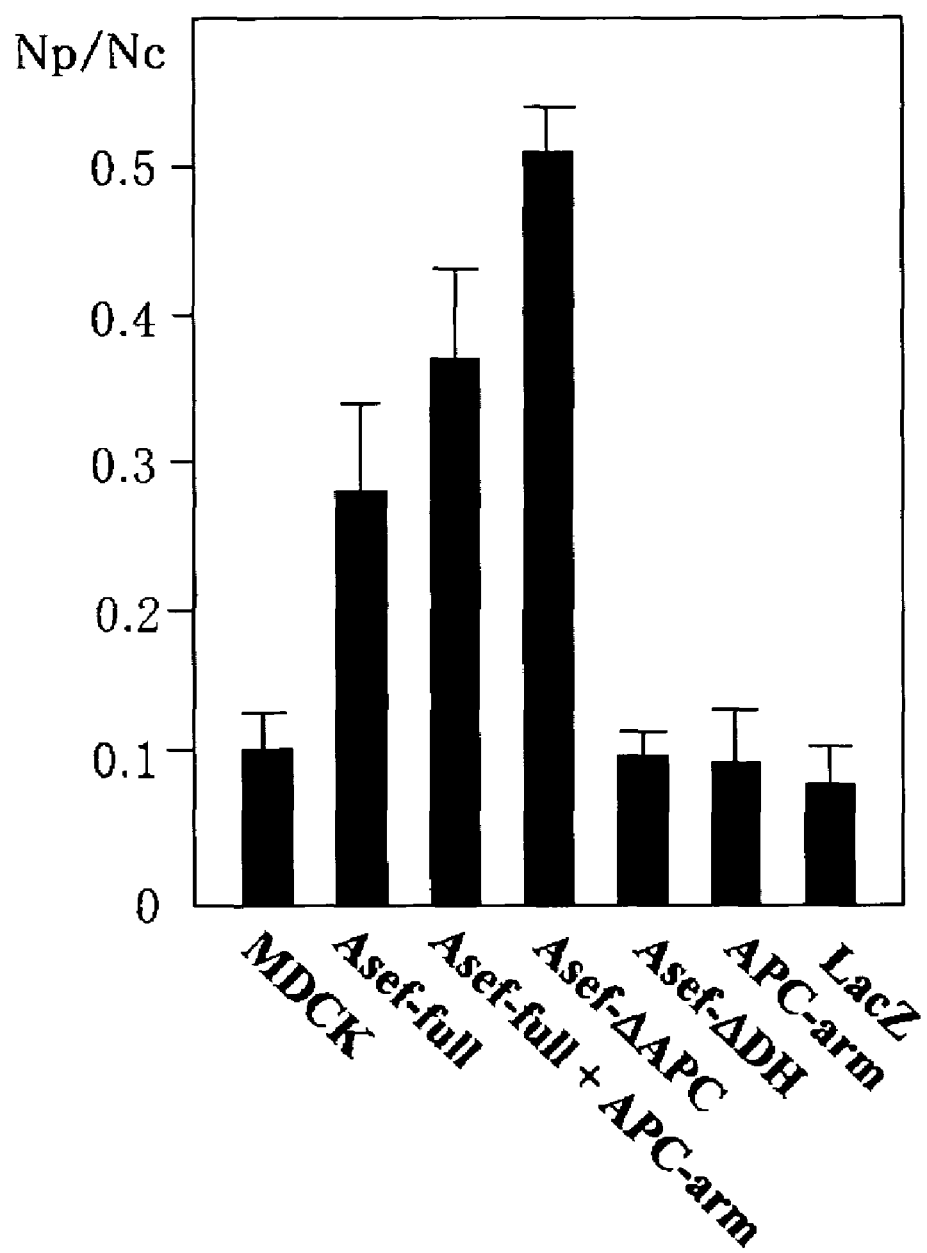
FIG. 1 illustrates decreased cell-cell adhesion of MDCK cells infected with adenoviruses that contains DNA encoding Asef. As shown in the vertical axis, cell-cell adhesion is represented by a numerical value obtained by dividing the number of cell clumps (Np) by the total number of cells (Nc). Cells were infected with adenoviruses containing a gene encoding full-length Asef (denoted by "Asef-full"), a gene encoding the armadillo repeat domain of the APC (denoted by "APC-arm"), a gene encoding an Asef mutant that lacks the APC-binding region (denoted by "Asef-ΔAPC"), or a gene encoding an Asef mutant that lacks the DH domain (denoted by "Asef-ΔDH"), as shown in the figure. The results are shown as mean±standard deviation (SD) obtained over three independent experiments.

The present invention claims the benefit of priority from Japanese Patent Application No. 2002-382083, which is incorporated herein by reference in its entirety.

Technical and scientific terms used herein have the meanings as normally understood by those skilled in the art, unless otherwise defined. Various methods that are well known to those skilled in the art are referenced herein. These reference materials, such as published materials disclosing known methods cited herein, are incorporated herein by reference in their entirety.

Embodiments of the present invention are explained in further detail below. However, the detailed description below is exemplary and for the purpose of explanation only, and is not intended to limit the scope of the present invention.

In the present invention, it was found that Asef decreases cell-cell adhesion of epithelium-derived cells and also noticeably promotes the motility thereof. Further, it was found that these functions are regulated by APC, and particularly, it was found that truncated APC mutants that are identified in the majority of colorectal tumor cells activate Asef constitutively. Therefore, it is believed that formation of a complex between mutated APC and Asef contributes to aberrant motility of colorectal tumor cells. That is, it is concluded that the complex may be involved in the upward migration of intestinal epithelial cells, more specifically, in the migration from the crypt to the villus tip. Indeed, it has been reported that forced expression of the APC gene induces aberrant cell migration in the intestinal epithelium (Non-patent Reference 11). It has been reported that early adenoma cells in APC knockout mice exhibit a proliferation rate similar to that of normal crypt epithelial cells, but lack directed migration along the crypt-villus axis (Non-patent Reference 12).

Aberrant migratory behavior due to Asef activation by truncated APC mutants may be thus significant for both adenoma formation and tumor progression to invasive malignancy. In addition, Asef mutants that lack the GEF domain do not decrease cell-cell adhesion or do not promote cell motility, resulting in the conclusion that GEF activity is important for such a function of Asef.

In the present invention, it was revealed that the motility of colorectal tumor cells expressing mutant APCs can be inhibited by using a dominant-negative mutant that inhibits the binding of Asef to mutant APCs, for example, a mutant consisting of the APC-binding region (amino acid sequence from the $73^{rd}$ to the $126^{th}$ amino acid residue) in the amino acid sequence of Asef or a mutant that lacks the GEF domain of Asef. Also revealed was that the motility of colorectal tumor cells expressing mutant APCs can similarly be inhibited by inhibiting the expression of the Asef gene or the APC gene. Further, it was found in an in vivo study using severe combined immunodeficient mice (SCID mice) that the tumorigenicity, proliferative growth and, moreover, metastasis of human colorectal tumor cells expressing the aforementioned dominant-negative mutants are inhibited in comparison to those of the cells that do not express the mutants. Such an inhibition was observed similarly in a study using cells that were obtained by cloning after expression of the mutants as human colorectal tumor cells expressing the dominant-negative mutants, and also in a study (mixed-population method) using a mixed population that was obtained from cells transformed with the labeled mutants by using a cell sorter to concentrate the cells expressing the mutants to a density of 90% or more employing the label as an indicator.

The inhibition of the function of Asef thus makes it possible to inhibit the motility of cells and, further, to inhibit tumorigenicity of cells and proliferative growth and/or metastasis of tumor cells. Since the inhibition of cell motility can also be achieved by inhibiting the expression of the Asef gene or the APC gene, it is possible to inhibit tumorigenicity of cells and proliferative growth and/or metastasis of tumor cells by inhibiting the expression of each these genes.

Based on the above-described findings, the present invention provides an agent for inhibiting metastasis of colorectal cancer and a method for inhibiting metastasis of colorectal cancer, which are characterized by inhibiting the function of Asef. The agent for inhibiting metastasis of colorectal cancer and the method for inhibiting metastasis of colorectal cancer are characterized by inhibiting the function of Asef and/or inhibiting the expression of the Asef gene.

Inhibition of the expression of the Asef gene can be carried out, for example, by applying an RNA interference effect on the expression of the Asef gene. RNA interference is a method for inhibiting the expression of a gene by using RNA, as has been reported in recent years (Non-patent Reference 13). More specifically, the expression of the Asef gene can be inhibited by using an oligonucleotide that exhibits an RNA interference effect on the expression of the Asef gene. Examples of the oligonucleotide can include a cDNA having the nucleotide sequence set forth in SEQ ID NO: 1 in the sequence listing. The complementary RNA (SEQ ID NO: 3 in the sequence listing) of the cDNA can also be used. Inhibition of the expression of the Asef gene can be carried out by transfecting a cell with a vector containing the cDNA or with the complementary RNA thereof. Transfection of a cell with the vector or with the RNA can be conducted utilizing a known method such as lipofection. Accordingly, an agent for inhibiting Asef comprising the aforementioned oligonucleotide is also included in the scope of the present invention. The agent for inhibiting Asef may contain one kind of oligonucleotide, or may contain two or more kinds of oligonucleotide. Further, inhibition of the Asef gene expression may also be carried out by using an antisense oligonucleotide against the Asef gene. The aforementioned oligonucleotide exhibiting an RNA interference effect or the aforementioned antisense oligonucleotide can be obtained from oligonucleotides that are designed on the basis of the nucleotide sequence of the Asef gene, by selecting oligonucleotides that specifically inhibit the expression of Asef using an Asef gene expression system.

Inhibition of the function of Asef can be carried out, for example, by inhibiting the binding of Asef to APC, or inhibiting the GEF activity of Asef. The binding of Asef to APC, which is the target of inhibition, is preferably the binding of Asef to normal APC, more preferably the binding of Asef to an APC mutant, further preferably the binding of Asef to a truncated APC mutant, and still more preferably the binding of Asef to a truncated APC mutant that contains an armadillo repeat domain. Examples of a truncated APC mutant that contains an armadillo repeat domain include a polypeptide consisting of the consecutive amino acid residues from the $1^{st}$ (the N terminus) to the $876^{th}$ residue of the amino acid sequence of APC, or a polypeptide consisting of the consecutive amino acid residues from the $1^{st}$ (the N terminus) to the $1309^{th}$ residue of the amino acid sequence of APC. These polypeptides were identified as truncated APC mutants in most colorectal cancers and familial adenomatous polyposis (FAP).

Inhibition of the binding of Asef to APC can be carried out using a dominant-negative Asef mutant for the binding. For example, an Asef mutant that can bind to APC but does not exhibit GEF activity can be used as an agent for inhibiting the binding of Asef to APC. Such an Asef mutant can be obtained by designing mutants based on the amino acid sequence of Asef and examining their binding activity to APC according to a conventional method. More specifically, a mutant that lacks the GEF domain of Asef can be exemplified. Alternatively, a polypeptide consisting of the APC-binding region (amino acid sequence from the $73^{rd}$ to the $126^{th}$ amino acid residue) in the amino acid sequence of Asef is preferably used. A polypeptide that inhibits the binding of Asef to APC that is selected from polypeptides that are designed based on the amino acid sequence of this polypeptide, can also be used. Further, inhibition of the binding of Asef to APC can also be carried out by inhibiting the expression of the APC gene. Inhibition of APC gene expression can be conducted by using an oligonucleotide that exhibits an RNA interference effect on the expression of the APC gene. Examples of the oligonucleotide can include a cDNA having the nucleotide sequence set forth in SEQ ID NO: 2 in the sequence listing. Further, the complementary RNA (SEQ ID NO: 4 in the sequence listing) of the cDNA can also be used. Alternatively, inhibition of the APC gene expression can be carried out by using an antisense oligonucleotide against the APC gene. The aforementioned oligonucleotide exhibiting an RNA interference effect or the aforementioned antisense oligonucleotide can be obtained from oligonucleotides that are designed on the basis of the nucleotide sequence of the APC gene, by selecting oligonucleotides that specifically inhibit the expression of APC using an APC gene expression system.

Inhibition of the GEF activity of Asef can be carried out, for example, by using an inhibitor of GEF activity that can be identified using Asef. Further, a compound that inhibits the expression of the Asef gene or a compound that inhibits the binding of Asef to APC may be identified using the Asef gene or using Asef and APC, and the thus-identified compound may be used. An assay system for identifying the compound can be constructed utilizing a known screening system.

Metastasis of colorectal cancer can be inhibited by using an agent for inhibiting Asef that contains the above-described substance that inhibits the function and/or the expression of Asef as an active ingredient. That is, an agent for inhibiting metastasis of colorectal cancer comprising an agent for inhibiting Asef and a method for inhibiting metastasis of colorectal cancer comprising using the aforementioned agent for inhibiting Asef are also included in the scope of the present invention. More specifically, an agent for inhibiting metastasis of colorectal cancer comprising an oligonucleotide having any one of the nucleotide sequences set forth in SEQ ID NOS: 1 to 4 in the sequence listing and a method for inhibiting metastasis of colorectal cancer comprising using at least one of these oligonucleotides can be exemplified.

Tumorigenicity and metastasis of colorectal cancer can be inhibited by applying the agent for inhibiting metastasis of colorectal cancer or the agent for inhibiting Asef of the present invention. More specifically, the above described agent for inhibiting metastasis of colorectal cancer or the agent for inhibiting Asef can be used in the prevention and/or treatment of colorectal cancer and colorectal cancer metastasis. From this viewpoint, an agent for preventing and/or treating colorectal cancer comprising an effective amount of the aforementioned agent for inhibiting metastasis of colorectal cancer or the agent for inhibiting Asef as an active ingredient are also included in the scope of the present invention. Further, a method for preventing and/or treating colorectal cancer comprising using the aforementioned agent for inhibiting metastasis of colorectal cancer or the agent for inhibiting Asef can be also provided.

A pharmaceutical composition that includes the aforementioned agent for inhibiting metastasis of colorectal cancer or the agent for inhibiting Asef can be thus provided according to the present invention.

Suitable dosage ranges of the pharmaceutical composition of the present invention can be can be determined according to the following: effectiveness of the ingredients contained therein; the route of administration; the properties of the prescription; the characteristics of the symptoms of the subject; and the judgment of the physician in charge. In general, a suitable dosage may fall, for example, within a range of approximately 0.01 µg to 100 mg per 1 kg of the body weight of the subject, and preferably within a range of approximately 0.1 µg to 1 mg per 1 kg. However, a dosage may be altered using conventional experiments for optimization of a dosage that are well known in the art. The aforementioned dosage can be divided for administration once to several times a day. Alternatively, periodic administration once every few days or few weeks can be employed.

When using an oligonucleotide that is capable of inhibiting the expression of the Asef gene or APC gene, it is possible to produce the oligonucleotide into the cell of the target by use of gene therapy. The gene therapy can be performed by using a known method. For example, a non-viral transfection comprising administering the oligonucleotide directly by injection and a transfection using a virus vector can both be applied. A method is recommended for non-viral transfection that comprises administering a phospholipid vesicle such as a liposome that contains the oligonucleotide, as well as a method comprising administering the oligonucleotide directly by injection. A liposome for use in this method can be more preferably exemplified by a cationic liposome. A vector used for a transfection using a virus vector, into which the oligonucleotide is incorporated, can be preferably exemplified by a DNA virus vector such as a retrovirus vector, an adenovirus vector, an adeno-associated virus vector and a vaccine virus vector, or a RNA virus vector. Use of these virus vectors enables administration to be carried out effectively. Further, a method is recommended for a transfection using a virus vector that comprises administering a phospholipid vesicle such as a liposome that contains the vector.

A medicament of the present invention can be prepared as a medicament that contains only an active ingredient of the agent for inhibiting metastasis of colorectal cancer or the agent for inhibiting Asef, but it is ordinarily prepared as a pharmaceutical composition using one or more kinds of a pharmaceutical carrier.

The amount of the active ingredient contained in the pharmaceutical formulation of the present invention can be appropriately selected from a broad range. In general, a suitable amount may fall within a range of approximately 0.00001 to 70 wt %, preferably approximately 0.0001 to 5 wt %.

Examples of the pharmaceutical carrier include a diluent or excipient such as a filler, expander, binder, wetting agent, disintegrator, surfactant, or lubricant that are normally used in accordance with the form of use of the formulation, and these can be suitably selected and used in accordance with the administration route of the formulation to be obtained. Examples of the carrier include physiological saline, buffered physiological saline, dextrose, water, glycerol, ethanol, and mixtures thereof. A carrier is not limited to these examples, and any substance can be used according to one's desire as long as the substance can be used for formulation of a common medicament.

The pharmaceutical composition of the present invention can be used as a solution formulation. It can also be used as a lyophilized formulation in order to preserve it, which can be used by dissolving it in water or in a buffered solution including physiological saline or the like to prepare it to a suitable concentration just before use.

When administering the pharmaceutical composition of the present invention, the pharmaceutical composition may be used alone or may be used together with other compounds or medicaments necessary for the treatment.

In terms of a route of administration, it may be either systemic administration or local administration. The route of administration that is appropriate for a particular disease or symptomatic conditions should be selected. As examples, parenteral administration including normal intravenous injection, intraarterial administration, subcutaneous administration, intracutaneous administration and intramuscular administration can be employed. Oral administration can be also employed. Further, transmucosal administration or dermal administration can be employed. Direct administration to the neoplasm by an injection or the like can be employed.

In terms of an administration form, various forms can be selected from administration forms that are known to those skilled in the art, and typical examples thereof include an administration form of a solid formulation such as a tablet, pill, powder, powdered drug, fine granule, granule, or capsule, as well as an administration form of a liquid formulation such as an aqueous formulation, ethanol formulation, suspension, fat emulsion, liposome formulation, clathrate such as cyclodextrin, syrup, or an elixir. These can be further classified according to the administration route into an oral formulation, parenteral formulation (drip injection formulation or injection formulation), nasal formulation, inhalant formulation, transvaginal formulation, suppositional formulation, sublingual agents, eye drop formulation, ear drop formulation, ointment formulation, cream formulation, transdermal absorption formulation, transmucosal absorption formulation and the like, which can be respectively blended, formed and prepared according to conventional methods.

In general, when using the pharmaceutical composition of the present invention for gene therapy, the pharmaceutical composition is preferably prepared as an injection formulation, drip injection formulation or liposome formulation. The pharmaceutical composition can also be prepared in a form that allows administration thereof together with a substance that enhances the efficiency of gene transfer, such as protamine.

Powders, pills, capsules, and tablets can be prepared using an excipient such as lactose, glucose, sucrose, or mannitol; a disintegrate agent such as starch or sodium alginate; a lubricant such as magnesium stearate or talc; a binder such as polyvinyl alcohol, hydroxypropyl cellulose, or gelatin; a surfactant such as fatty acid ester; a plasticizer such as glycerin, and the like. For preparation of a tablet or a capsule, a pharmaceutical carrier in a solid state is used.

A suspension can be prepared using water; sugars such as sucrose, sorbitol, or fructose; glycols such as PEG; and oils.

Injectable solutions can be prepared using a carrier comprising a salt solution, a glucose solution or a mixture of salt water and a glucose solution.

Inclusion into a liposome formulation can be conducted in the following manner: by dissolving the substance of interest in a solvent (e.g., ethanol) to make a solution, adding a solution of phospholipids dissolved in an organic solvent (e.g., chloroform), removing the solvent by evaporation and adding a phosphate buffer thereto, agitating the solution and then subjecting it to sonication followed by centrifugation to obtain a supernatant, and finally, filtrating the supernatant to recover liposomes.

A fat emulsion can be prepared in the following manner: by mixing the substance of interest, an oil ingredient (vegetable oil such as soybean oil, sesame oil, olive oil, or MCT), an emulsifier (such as a phospholipid), and the like; heating the mixture to make a solution; adding water of a required quantity; and then emulsifying or homogenizing by use of an emulsifier (a homogenizer, e.g., a high pressure jet type, an ultrasonic type, or the like). The fat emulsion may be also lyophilized. For conducting lipid-emulsification, an auxiliary emulsifier may be added, and examples thereof include glycerin or saccharides (e.g., glucose, sorbitol, fructose, etc.).

Inclusion into a cyclodextrin formulation may be carried out in the following manner: by dissolving the substance of interest in a solvent (e.g., ethanol); adding a solution of cyclodextrin dissolved in water under heating thereto; chilling the solution and filtering the precipitates; and drying under sterilization. At this time, the cyclodextrin to be used may be appropriately selected from among those having different void sizes ($\alpha$, $\beta$, or $\gamma$ type) in accordance with the bulkiness of the substance of interest.

EXAMPLES

Hereinafter, the present invention may be explained more particularly with examples; however, the present invention is not limited to the following examples.

First, the following definitions relate to Asef, APC, and the mutants thereof that are used in the examples herein. The proteins and the mutants are referred to in abbreviated form.

Asef-full is a protein consisting of the wild-type, full-length Asef. It was expressed as a haemagglutinin (HA)-tagged fusion protein (HA-tagged wild-type Asef) or a Glutathione S-transferase (GST) fusion protein (GST-Asef-full).

Asef-ΔAPC is a mutant that lacks the N-terminal APC-binding region of Asef. This mutant possesses stronger GEF activity than wild-type Asef.

Asef-ΔDH is a mutant that lacks the DH domain (GEF domain) of Asef. This mutant does not exhibit GEF activity.

Asef-ABR is a polypeptide consisting of the APC-binding region (amino acid sequence from the $73^{rd}$ to the $126^{th}$ residue) in the amino acid sequence of Asef. It was expressed as a maltose-binding protein (MBP) fusion protein (MBP-Asef-ABR).

APC-arm is a polypeptide consisting of the armadillo repeat domain of APC. It was expressed as a Myc-tagged fusion protein (Myc-tagged APC-arm).

APC-876 is a polypeptide consisting of the consecutive amino acid residues from the $1^{st}$ (the N terminus) to the $876^{th}$ residue of the amino acid sequence of APC, which contains the armadillo repeat domain.

APC-1309 is a polypeptide consisting of the consecutive amino acid residues from the $1^{st}$ (the N terminus) to the $1309^{th}$ residue of the amino acid sequence of APC, which contains the armadillo repeat domain.

APC-876 and APC-1309 are truncated APC mutants that were identified in colorectal tumors and familial adenomatous polyposis (FAP).

Adenoviruses that contain DNA encoding any of these proteins or polypeptides were prepared by cloning polynucleotides that encode each protein into the pAdeno-X adenoviral vector using the Adeno-X™ Expression System (Clontech, Palo Alto, Calif.). The term "AdAsef-full" hereunder refers to an adenovirus that contains DNA encoding Asef-full. Adenoviruses that contain DNA encoding the other proteins or polypeptides described above are likewise represented hereunder by adding "Ad" to the designated name of each DNA.

Plasmids that contain DNA encoding any of the aforementioned proteins or polypeptides were prepared according to a conventional method.

Cell culture and transfection of the aforementioned plasmids were carried out as described in the following. MDCK cells (epithelial-like cell line established from a normal canine kidney) and WiDr cells were cultured in Dulbecco's modified Eagle's medium supplemented with 10% fetal calf serum (FCS). SW480 cells were cultured in Leibovitz's L-15 medium supplemented with 10% FCS. DLD-1 cells and HCT15 cells were cultured in RPMI 1640 medium supplemented with 10% FCS. HCT116 cells were cultured in McCoy's 5A medium supplemented with 10% FCS. These cells were transfected with the above-described plasmids using LipofectAMINE 2000 (Life Technologies, Carlsbad, Calif.).

Preparation and expression of proteins were carried out in the following manner. Proteins fused to GST or MBP were synthesized in *Escherichia coli* and isolated by absorption to glutathione Sepharose (GSH-Sepharose; Pharmacia, Buckinghamshire, UK) or amylose resin (New England Biolabs, Beverly, Mass.).

Short hairpin RNAs (hereunder, referred to in abbreviated form as "shRNA"), such as shRNA-Asef and shRNA-APC used in the RNA interference experiments were designed to inhibit the expression of the Asef gene and the APC gene, respectively. The nucleotide sequences of shRNA-Asef and shRNA-APC are set forth in SEQ ID NO: 1 and SEQ ID NO: 2 in the sequence listing, respectively. Further, mutations were added to shRNA-Asef and shRNA-APC to prepare shRNAs that did not inhibit the expression of the Asef gene and the APC gene. These are mut-shRNA-Asef and mut-shRNA-APC, which are set forth in SEQ ID NO: 5 and SEQ ID NO: 6 in the sequence listing, respectively.

EXAMPLE 1

In order to examine the effects of Asef on cell-cell adhesion and cell morphology, MDCK cells were infected with the above-described adenoviruses. The adenoviruses used were AdAsef-full, AdAsef-ΔAPC, AdAsef-ΔDH and AdAPC-arm. AdLacZ was used as a control. Immunofluorescence staining showed that the infection efficiency of the adenoviruses to MDCK cells was 90% or more. Immunoblot analysis showed that each of these viruses produces a protein of the expected size when infected into MDCK cells.

Cell morphology was examined as follows. Cells were planted in 12-well tissue culture plates to get $3.0 \times 10^4$ cells per well. After 3 h of incubation at 37° C., cells were infected with adenoviruses (multiplicity of infection (MOI)= 200), cultured for a further 36 h and then observed by a phase-contrast microscope. Cells infected with AdAsef-ΔAPC became flattened onto the substratum and exhibited membrane ruffles and lamellipodia. In contrast, cells infected with AdAsef-ΔDH showed no morphological changes and resembled uninfected cells.

Cell-cell adhesion was examined as follows. Infected cells were scraped from plates in phosphate-buffered saline (PBS) containing 0.02% ethylenediamine tetraacetic acid (EDTA) and subjected to pipetting 20 times. The number of cell clusters (particles) was then counted. The cell-cell adhesion was evaluated from a value obtained by dividing the number of cell clusters by the total number of cells (Np/Nc). When cells were dispersed by pipetting, cells infected with AdAsef-ΔAPC dissociated efficiently, whereas uninfected cells and cells infected with AdAsef-ΔDH or AdLacZ remained as clusters (FIG. 1). These results showed that Asef has a function to decrease cell-cell adhesion, and that its GEF activity is essential for this function.

Further, immunohistochemical analysis using an anti-E-cadherin antibody showed that overexpression of either AdAsef-full or AdAsef-ΔAPC resulted in decreased amounts of E-cadherin localized at the sites of cell-cell contact and enhanced amounts of E-cadherin localized in the cytoplasm. Immunohistochemical analysis was conducted as follows. After 36 h of adenovirus infection, MDCK cells were fixed with 3.7% formaldehyde in PBS. The fixed cells were double-stained with either a rat monoclonal antibody against E-cadherin (ECCD-2; Calbiochem, San Diego, Calif.) and trimethylrhodamine isothiocyanate-conjugated phalloidin (TRITC-conjugated phalloidin: Molecular Probes, Eugene Oreg.), or the rat monoclonal antibody against E-cadherin and a rabbit polyclonal antibody against β-catenin (SantaCruz Biotechnology, Santa Cruz, Calif.) for 60 min at room temperature. Staining patterns obtained with anti-E-cadherin antibody and anti-α-catenin antibody were visualized with fluorescein isothiocyanate-labelled anti-rat IgG antibody and TRITC-labelled anti-rabbit IgG antibody, respectively. The cells were photographed with a Carl Zeiss LSM510 laser scanning microscope. Staining with anti-β-catenin antibody showed a decreased amount of β-catenin localized at the site of cell-cell contact, although the decreased amount was not as prominent as that of E-cadherin. In contrast, cells infected with AdAsef-ΔDH or AdLacZ did not show any change in localization of E-cadherin or β-catenin. These results suggest that GEF activity of Asef is important for the changes in the localization of these molecules. Immunoblot analysis of MDCK cell lysates showed that the total amount of E-cadherin or β-catenin did not change significantly upon infection with AdAsef-full or AdAsef-ΔAPC. These results demonstrated that the decrease in cell-cell adhesion resulting from the expression of the Asef gene is due to a decrease in E-cadherin and β-catenin at the sites of cell-cell contact.

EXAMPLE 2

The effects of Asef on cell motility were examined using MDCK cells that were made to express the Asef gene, the APC gene, or mutant genes of these using the plasmids described above. Cell motility was examined by cell migration assays using Transwell migration chambers. The chambers used for MDCK cells were 12 mm in diameter with a pore size of 12 μm (Costar Corporation, Cambridge Mass.). After 18 h of transfection, $3.0 \times 10^4$ cells of MDCK cells were added to the upper compartment of the chamber and allowed to migrate toward the underside of the upper chamber for 18 h. Cell migration was determined by measuring the cells that had migrated to the lower side of the polycarbonate filters.

Figure 2:
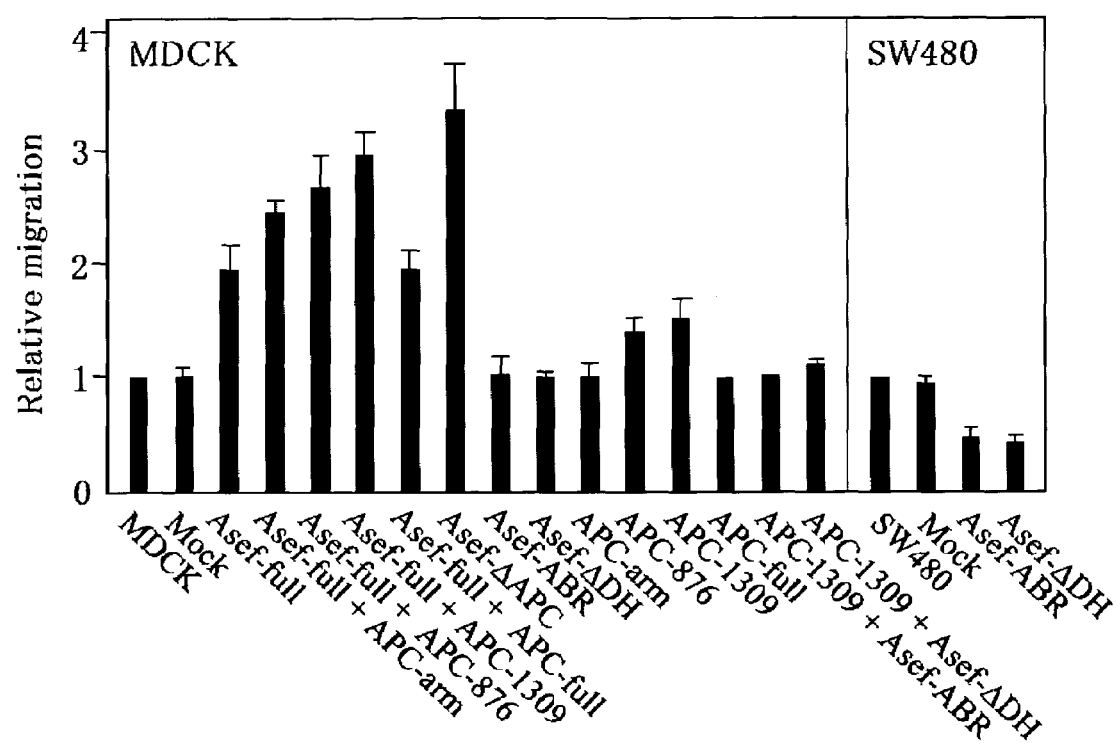
FIG. 2 illustrates that enhanced MDCK cell motility by the expression of the Asef gene was further increased by co-expression with an APC mutant that contains the armadillo repeat domain (APC-arm, APC-876 and APC-1309), while the enhanced motility by expression of the Asef gene, as well as the inherent cell motility, was decreased by expression of the Asef-ΔDH gene or the Asef-ABR (APC-binding region of Asef) gene. The results are shown as the relative migration as compared to that of the parental cells. The term "Mock" in the figure refers to cells transfected with an empty vector.

Cells infected with a plasmid that contains DNA encoding Asef-full showed enhanced motility as compared with parental cells (MDCK) or vector-transfected cells (Mock) (FIG. 2). Cells that were made to co-express the Asef-full gene together with any one of the APC-arm gene, the APC-876 gene and the APC-1309 gene were more motile than cells transfected with the Asef-full gene alone. In the effect of APC on the ability of Asef to promote cell-motility, APC-arm, APC-876 and APC-1309 were stronger than APC-full. In contrast, APC-arm alone did not promote migration. In addition, cells transfected with the Asef-ΔAPC gene showed a further enhanced migration reaction as compared with cells cotransfected with the Asef-full gene and the APC-arm gene. These results showed that Asef has the potential to promote the migration of MDCK cells. It was shown that this potential of Asef is further enhanced by APC, particularly a truncated APC mutant that contains an armadillo repeat domain (APC-Arm). In addition, Asef-ΔDH did not promote the migration of MDCK cells, indicating that the GEF activity of Asef is required for such migration stimulatory activity.

Meanwhile, when the Asef-ABR gene was expressed together with the APC-1309 gene, enhancement of cell migration was almost completely inhibited. Asef-ΔDH also inhibited APC-1309 mediated enhancement of cell migration. These results indicate that the APC mutants, APC-879 and APC-1309, which have been identified in colorectal cancers and FAP, interact with Asef, and enhance its activity, thereby promoting cell migration. On the other hand, when the full-length APC gene was transfected into MDCK cells, no enhancement of Asef-induced migration was observed (FIG. 2). This indicates that APC may not be an efficient activator of Asef until APC is activated by truncation in colorectal tumor cells.

Next, the motility of SW480 cells that are known to include Asef and truncated APC mutants was examined. When SW480 cells were transfected with plasmids that contain DNA encoding Asef-ABR, the migration of the cells decreased to about 50% of that of the parental cells or Mock cells (FIG. 2). Similarly, the migration of SW480 cells transfected with Asef-ΔDH plasmids decreased by to about 40%. These results demonstrated that Asef-ABR or Asef-ΔDH expressed in cells acts on the binding of Asef to truncated APC mutants in a dominant-negative manner, thereby inhibiting the cell migration.

EXAMPLE 3

The binding of Asef to truncated APC mutants in colorectal tumor cells was examined as follows. First, $5.0 \times 10^6$ cells of SW480 cells were lysed in 500 μl of buffer A (50 mM Tris-HCl (pH 7.5), 150 mM NaCl, 5 mM EDTA, 2 mM sodium vanadate ($Na_3VO_4$) and 10 mM sodium fluoride) containing 1% Triton X-100. The lysate was incubated with 2 μg of anti-Asef antibody for 1 h at 4° C., and then the immunocomplex was adsorbed to protein G-Sepharose 6B for 2 h at 4° C. After washing extensively with buffer A containing 1% Triton X-100, the sample was resolved by SDS-PAGE, and transferred to a polyvinylidene difluoride membrane filter (Immobilon P; Millipore, Bedford, Mass.). The blot was analyzed by immunoblot analysis using alkaline phosphatase-conjugated mouse anti-rabbit IgG antibody (Promega, Madison, Wis.) as a second antibody. The rabbit anti-Asef polyclonal antibody used was prepared by a conventional method (Non-patent Reference 1).

Figure 3A:
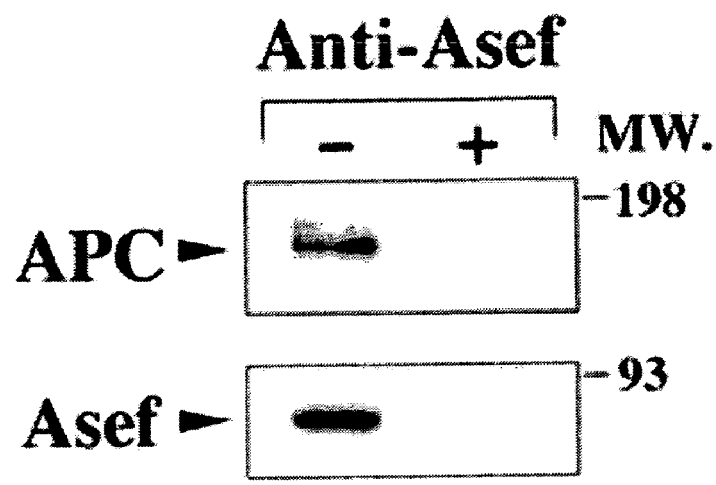
FIG. 3a illustrates the binding of Asef to truncated APC mutants in SW480 cells. Analysis of binding was carried out by immunoprecipitation using an anti-Asef antibody (Anti-Asef). In the figure, the symbol +indicates that the antibody used was pre-incubated with antigen before immunoprecipitation.

The results showed that Asef co-immunoprecipitated with the truncated APC mutant (FIG. 3a). Co-immunoprecipitation of Asef and the APC mutant was inhibited by preincubation of the antibody with an excess of the antigen for 2 h at 4° C. These results demonstrate that Asef is associated with APC mutants in SW480 cells.

Figure 3B:
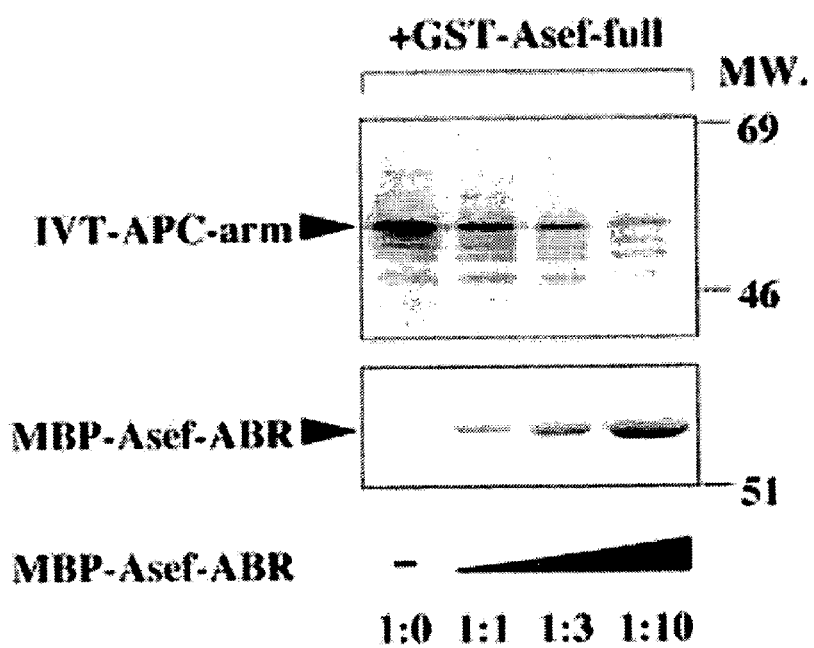
FIG. 3b illustrates that Asef-ABR (APC-binding region of Asef) inhibited the interaction of IVT-APC-arm with GST-Asef-full in vitro in a dose dependent manner. In the figure, "MW." represents a molecular marker.

Next, co-immunoprecipitation of GST-Asef-full and APC-arm was conducted in vitro to examine the effect of Asef-ABR addition. First, APC-arm was produced by in vitro translation (IVT-APC-arm), and incubated with GST-Asef-full bound to Sepharose in the presence of MBP-Asef-ABR. The relative amounts of APC-arm to MBP-Asef-ABR were varied as indicated in FIG. 3b. APC-arm bound to GST-Asef-full-Sepharose was visualized by SDS-PAGE followed by autoradiography (top panel of FIG. 3b). MBP-Asef-ABR added to the reaction mixture was visualized by subjecting the gel to Coomassie blue staining (bottom panel of FIG. 3b). The results showed that the amount of co-immunoprecipitate of APC-arm and GST-Asef-full decreased in a dose-dependent manner along with the increasing amounts of Asef-ABR added. More specifically, it was revealed that Asef-ABR inhibits the binding of Asef to the APC mutant in vitro.

The inhibition of the migration of SW480 cells was achieved using Asef-ABR that inhibits the binding of Asef to the APC mutant in a dominant negative manner.

EXAMPLE 4

Various colorectal tumor cell lines were infected with adenoviruses that contain DNA encoding Asef-full, Asef-ΔAPC or Asef-ΔDH, and assessed by cell migration assays in the same manner as in Example 2. The colorectal tumor cell lines used were SW480, DLD-1, HCT15, WiDr and HCT116. SW480 cells, DLD-1 cells, HCT15 cells and WiDr cells contain truncated APC mutants. HCT116 cells contain normal APC but mutated β-catenin.

Figure 4:
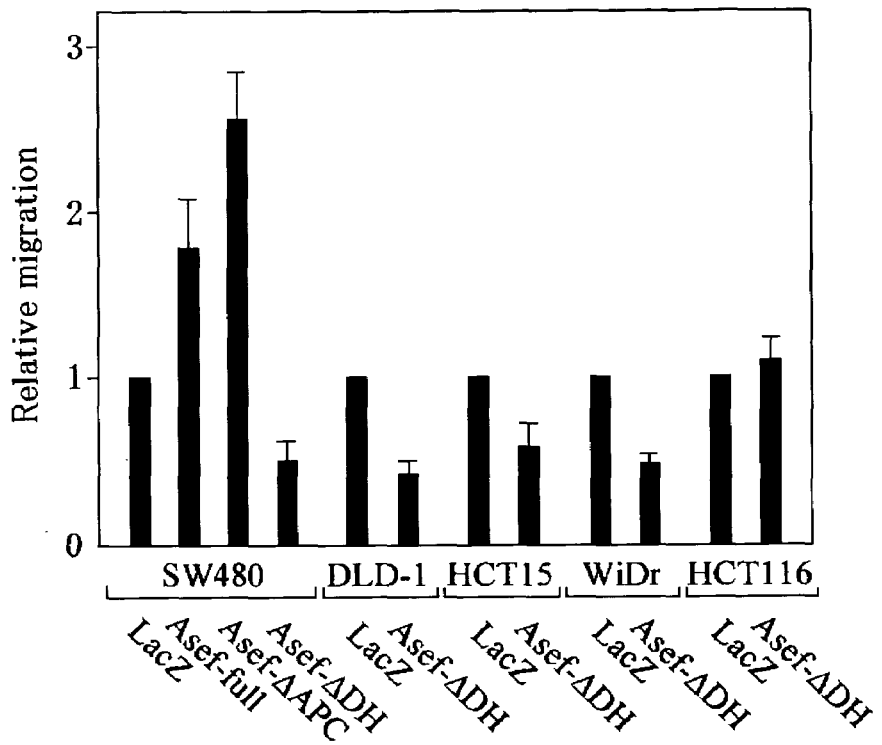
FIG. 4 illustrates that the motility of colorectal tumor SW480 cells is enhanced by expression of the Asef gene or the gene encoding Asef that lacks the APC-binding region (Asef-ΔAPC), while the motility of various colorectal tumor cells (SW480, DLD-1, HCT15, WiDr and HCT116) did not change or decreased when the gene encoding Asef lacking the GEF domain (Asef-ΔDH) was expressed. The results are shown as the relative migration as compared to that of each cell expressing the LacZ gene as a control.

The results are shown in FIG. 4. When SW480 cells were infected with AdAsef-full or AdAsef-ΔAPC, their motility was enhanced. Further, when SW480 cells, DLD-1 cells, HCT15 cells and WiDr cells were infected with AdAsef-ΔDH, their motility was partially inhibited. In contrast, the motility of HCT116 cells was not inhibited by AdAsef-ΔDH. This indicates that full-length APC in HCT116 is unable to induce the activation of Asef. These results demonstrated that the activation of Asef is induced in colorectal tumor cells that contain truncated APC mutants, while the activation of Asef is not or is hardly induced in cells that contain normal APC. The results also showed that the activation is inhibited by Asef-ΔDH.

EXAMPLE 5

The interaction of Asef with APC mutants in the migration of colorectal tumor cells was investigated using RNA interference experiments. The experiments were carried out using the pSHAG-1 vector system (Non-patent Reference 13). The colorectal tumor cell lines used were SW480 cells, WiDr cells, LS180 cells and HCT116 cells. SW480 cells and WiDr cells contain truncated APC mutants. LS180 cells and HCT116 cells contain normal APC but mutated β-catenin.

Figure 5:
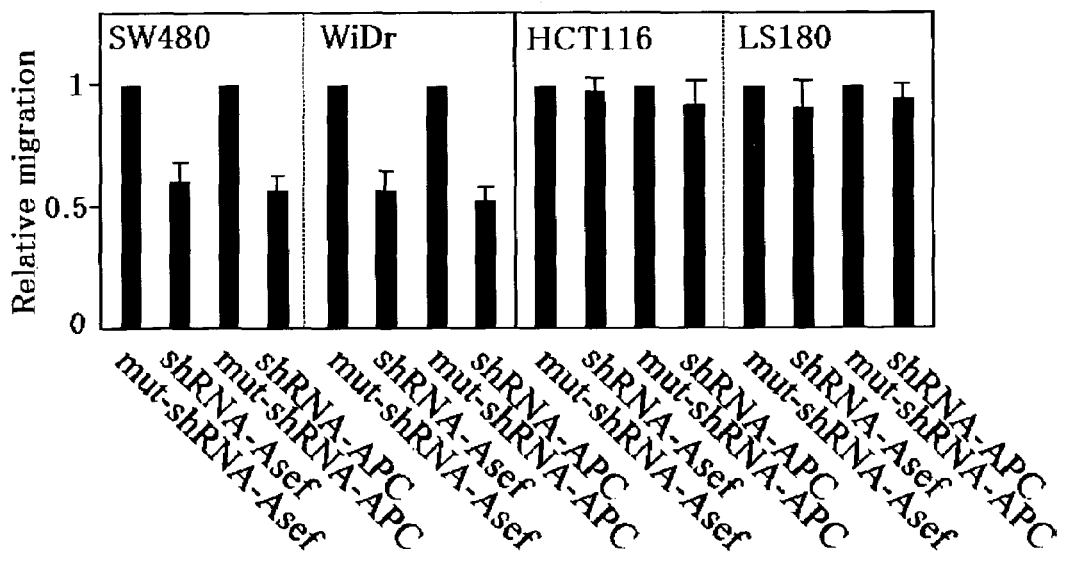
FIG. 5 illustrates that the short hairpin RNAs, shRNA-Asef and shRNA-APC which inhibit the expression of the Asef gene and the APC gene respectively, both decreased the motility of colorectal tumor cells having an APC mutation (SW480 and WiDr), while no effect was observed on the motility of colorectal tumor cells having normal APC (HCT116 and LS180). As controls for comparison, the short hairpin RNAs, mut-shRNA-Asef and mut-shRNA-APC, which do not inhibit the expression of Asef gene or APC gene, were used. The results are shown as the relative migration as compared to that of each cell transfected with mut-shRNA-Asef.

Cell migration assays were carried out in the same manner as in Example 2 to assess various colorectal tumor cells transfected with expression vectors that contain either shRNA-Asef or shRNA-APC. The results showed that SW480 cells and WiDr cells that were transfected with either shRNA-Asef or shRNA-APC exhibited decreased motility as compared with cells that were transfected with mut-shRNA-Asef or mut-shRNA-APC (FIG. 5). In contrast, this phenomenon was not observed in LS180 cells and HCT116 cells.

Next, immunoblot analysis was carried out in the same manner as in Example 3 to assess cells transfected with expression vectors that contain oligonucleotides encoding any one of shRNA-Asef, shRNA-APC, mut-shRNA-Asef and mut-shRNA-APC. Meanwhile, changes in α-tubulin were measured as a control. The results showed that shRNA-Asef and shRNA-APC almost completely inhibited the expression of the Asef gene and the APC gene, respectively.

It was thus demonstrated that the motility of colorectal tumor cells that contain truncated APC mutants is decreased by inhibiting the expression of the Asef gene or the APC gene. More specifically, the results indicated that interaction of Asef with APC mutants plays an important role in the migration of colorectal tumor cells.

EXAMPLE 6

Cells prepared by making the Asef dominant-negative mutant Asef-ABR express in human SW480 colorectal tumor cells were respectively transplanted to SCID mice to observe changes in their tumorigenicity or proliferation. Asef-ABR plasmids were transfected into SW480 colorectal tumor cells by lipofection. The thus-obtained 3 clones were respectively cultured in vitro using L-15 medium containing G418 at a final concentration of 1 mg/ml, and then transplanted subcutaneously in the flanks of 8-week-old SCID mice at $1 \times 10^7$ cells/0.1 ml/mouse (2 to 4 individuals per group). Twenty days after transplanting the tumor cells, tumor lumps were excised to measure their weights. The weight of tumor lumps (T) of each mouse that was transplanted with the clone was divided by the value of a control group (C) to get an inhibition ratio (abbreviated as "IR") that was expressed as a percentage [IR (%)=T/C×100]. The expression of Asef-ABR in the transplanted cells was confirmed by a conventional method.

Decreased tumorigenicity or delayed proliferation was seen in 2 out of 3 clones stably expressing Asef-ABR alone (Table 1). Thus, it is believed that Asef participates in tumorigenicity or tumor cell proliferation.

TABLE 1

| group | weight ± SD (g) | IR (%) | number of mice with tumor/transplanted with tumor |
|---|---|---|---|
| SW480 | 0.496 ± 0.080 | 0 | 4/4 |
| ABR-2 | 0.609 ± 0.069 | −22.7 | 3/3 |
| ABR-8 | 0.000 ± 0.000 | 100 | 0/3 |
| ABR-17 | 0.203 ± 0.056 | 59.1 | 4/4 |

EXAMPLE 7

Asef-ABR clones (see Example 6) that were prepared using the human HT29 colorectal tumor cell line were transplanted into SCID mice to observe changes in their tumorigenicity or proliferation. 15 μg of Asef-ABR plasmids were transfected into $5 \times 10^6$ cells of HT29 cells by lipofection. The thus-obtained 5 clones were respectively cultured in vitro using DMEM medium containing G418 at a final concentration of 1 mg/ml, and then transplanted into the spleen of 8-week-old SCID mice at $1 \times 10^6$ cells/0.05 ml/mouse (4 individuals per group). Eighteen days after transplanting the tumor cells, the mice were injected with ink via tail vein, and then sacrificed with bleeding under anesthesia with ether. The spleen and the liver were excised to measure their weights.

Tumor formation in the spleen and the liver was not observed in 4 out of 5 clones that are the stable transfectant expressing Asef-ABR dominant-negative mutant, which were prepared using HT29 cells (Table 2). The same phenomenon was also observed in 3 clones prepared in Example 6 using SW480 colorectal tumor cells. Thus, it was demonstrated that Asef participates in tumorigenicity and tumor cell proliferation. Further, no tumor formation in the liver was observed when using the stable transfectant expressing Asef-ABR dominant-negative mutant, indicating that Asef-ABR dominant-negative mutants inhibit tumor metastasis.

TABLE 2

| group | liver weight ± SD (g) | spleen weight ± SD (mg) |
|---|---|---|
| normal | 1.340 ± 0.176 | 30.8 ± 7.1 |
| parental cell line (HT29) | 2.236 ± 0.153 | 124.5 ± 20.4 |
| Asef-ABR-A7 | 1.584 ± 0.093 | 38.0 ± 3.9 |
| Asef-ABR-B5 | 2.627 ± 0.392 | 129.3 ± 13.5 |
| Asef-ABR-C3 | 1.579 ± 0.124 | 44.3 ± 11.0 |
| Asef-ABR-C12 | 1.526 ± 0.070 | 37.8 ± 5.1 |
| Asef-ABR-D11 | 1.359 ± 0.173 | 37.3 ± 4.6 |

INDUSTRIAL APPLICABILITY

In the present invention, it was found that Asef enhances the motility of cells, and that it decreases cell-cell adhesion, and that this function of Asef is activated by the gene product of the tumor suppressor gene APC. Further, it was found that Asef enhances the motility of the colorectal tumor cells and participates in the tumorigenicity and metastasis thereof in colorectal cancers, particularly in colorectal cancers in which mutant APCs are observed. According to the present invention based on these findings, the agent for inhibiting metastasis of colorectal cancer and the method for inhibiting metastasis of colorectal cancer, which inhibit the function of Asef and/or inhibit the expression of Asef gene, were provided. These inventions have a significant effect for the prevention and/or treatment of colorectal cancer and colorectal cancer metastasis.

SEQUENCE LISTING FREE TEXT

SEQ ID NO: 1: Designed oligonucleotide based on the nucleotide sequence of human Asef to inhibit the expression of the Asef gene.

SEQ ID NO: 2: Designed oligonucleotide based on the nucleotide sequence of human APC to inhibit the expression of the APC gene.

SEQ ID NO: 3: Designed oligonucleotide based on the nucleotide sequence of human Asef to inhibit the expression of the Asef gene.

SEQ ID NO: 4: Designed oligonucleotide based on the nucleotide sequence of human APC to inhibit the expression of the APC gene.

SEQ ID NO: 5: Designed oligonucleotide based on the nucleotide sequence set forth in SEQ ID NO: 1.

SEQ ID NO: 6: Designed oligonucleotide based on the nucleotide sequence set forth in SEQ ID NO: 2.

```
                        SEQUENCE LISTING

<160> NUMBER OF SEQ ID NOS: 6

<210> SEQ ID NO 1
<211> LENGTH: 31
<212> TYPE: DNA
<213> ORGANISM: Artificial
<220> FEATURE:
<223> OTHER INFORMATION: Designed oligonucleotide based on the
      nucleotide sequence of human Asef to inhibit the expression of the
      Asef gene

<400> SEQUENCE: 1
aagccgactt ccagatctac tcggagtact g                              31

<210> SEQ ID NO 2
<211> LENGTH: 31
<212> TYPE: DNA
<213> ORGANISM: Artificial
<220> FEATURE:
<223> OTHER INFORMATION: Designed oligonucleotide based on the
      nucleotide sequence of human APC to inhibit the expression of the
      APC gene

<400> SEQUENCE: 2
aactgaggca tctaatatga aggaagtact t                              31

<210> SEQ ID NO 3
<211> LENGTH: 31
<212> TYPE: RNA
<213> ORGANISM: Artificial
<220> FEATURE:
<223> OTHER INFORMATION: Designed oligonucleotide based on the
      nucleotide sequence of human Asef to inhibit the expression of the
      Asef gene

<400> SEQUENCE: 3
uucggcugaa ggucuagaug agccucauga c                              31

<210> SEQ ID NO 4
<211> LENGTH: 31
<212> TYPE: RNA
<213> ORGANISM: Artificial
<220> FEATURE:
<223> OTHER INFORMATION: Designed oligonucleotide based on the
      nucleotide sequence of human APC to inhibit the expression of the
      APC gene

<400> SEQUENCE: 4
uugacuccgu agauuauacu uccuucauga a                              31
```

```
<210> SEQ ID NO 5
<211> LENGTH: 31
<212> TYPE: DNA
<213> ORGANISM: Artificial
<220> FEATURE:
<223> OTHER INFORMATION: Designed oligonucleotide based on the
      nucleotide sequence set forth in SEQ ID NO: 1

<400> SEQUENCE: 5
aagacgactt ccaaatctac tcagagtact g                                31

<210> SEQ ID NO 6
<211> LENGTH: 31
<212> TYPE: DNA
<213> ORGANISM: Artificial
<220> FEATURE:
<223> OTHER INFORMATION: Designed oligonucleotide based on the
      nucleotide sequence set forth in SEQ ID NO: 2

<400> SEQUENCE: 6
aactaaggca tataatatga aggaaatact t                                31
```

What is claimed is:

1. An oligonucleotide consisting of the nucleotide sequence set forth in SEQ ID NO: 1 in the sequence listing.

\* \* \* \* \*